United States Patent [19]
Hale et al.

[11] Patent Number: 5,608,167
[45] Date of Patent: Mar. 4, 1997

[54] MEMBRANE-ENCLOSED SENSOR, FLOW CONTROL ELEMENT AND ANALYTIC METHOD

[75] Inventors: John M. Hale, Meinier; Eugen Weber, Hinwil, both of Switzerland

[73] Assignee: Orbisphere Laboratories Neuchâtel SA, Neuchâtel, Switzerland

[21] Appl. No.: 390,980

[22] Filed: Feb. 21, 1995

[51] Int. Cl.⁶ .................................................. G01L 7/08
[52] U.S. Cl. .................................................. 73/715; 73/700
[58] Field of Search ........................... 73/700, 715, 742, 73/23.2, 23.35

[56] References Cited

U.S. PATENT DOCUMENTS

| | | | |
|---|---|---|---|
| 3,789,666 | 2/1974 | Favre | 73/702 |
| 4,019,863 | 4/1977 | Jenkins et al. | 73/863.23 |
| 4,096,047 | 6/1978 | Hale et al. | |
| 4,409,849 | 10/1983 | Roos | 73/864 |
| 4,906,339 | 3/1990 | Hale | |
| 4,918,975 | 4/1990 | Voss | 73/40.7 |
| 5,037,737 | 8/1991 | Liffmann et al. | 435/11 |
| 5,144,831 | 9/1992 | Hale et al. | |
| 5,331,845 | 7/1994 | Bals et al. | 73/61.43 |
| 5,400,665 | 3/1995 | Zhu et al. | 73/863.23 |

FOREIGN PATENT DOCUMENTS

| | | |
|---|---|---|
| 0043611B1 | 2/1985 | European Pat. Off. . |
| 0293541B1 | 2/1992 | European Pat. Off. . |
| 0429396B1 | 6/1994 | European Pat. Off. . |

*Primary Examiner*—Richard Chilcot
*Assistant Examiner*—Max H. Noori
*Attorney, Agent, or Firm*—Wigman, Cohen, Leitner & Myers, P.C.

[57] ABSTRACT

A membrane-enclosed sensor (1) of the type having a membrane (11) for exposure to a fluid external phase of analytical interest at an interface between the fluid external phase or sample, and said membrane; the sensor comprises a coiled, e.g. spiraloid, channel (15) at the interface; the channel has an inlet end (16) as well as an outlet end (18) for passing the external phase in contact with the membrane along said coiled channel which, preferably has a length which is at least about 5 times greater than the largest cross dimension of the membrane.

19 Claims, 1 Drawing Sheet

MEMBRANE-ENCLOSED SENSOR, FLOW CONTROL ELEMENT AND ANALYTIC METHOD

BACKGROUND OF THE INVENTION

1. Field of the Invention

The invention generally relates to the analytical art and specifically to membrane-enclosed sensors for use in various methods of analysis.

2. Description of the Prior Art

Membrane-enclosed sensors (also termed MES herein for short) are a known species of analytical devices frequently used for determining the concentration of an analytical species of interest in a fluid sample. One type of MES (a membrane-enclosed amperometric sensor or cell also termed "Clark Cell") is disclosed e.g. in U.S. Pat. No. 4,096,047, and the art mentioned therein, and is used in amperometric (also termed "polarographic" or "voltaic") analyses. Another type (a membrane-enclosed sensor sensitive to the flow rate of an analytical species through the membrane) is disclosed e.g. in U.S. Pat. No. 5,144,831 and EP-A-0429396 and the art discussed therein. Membrane separators for mass spectrophotometric, gas chromatographic and other techniques represent yet a further type of MES.

Generally, the membrane of an MES serves to separate a fluid substance (termed "external phase" herein) containing a species of analytical interest (also termed "analyte" herein) from a sensing means within the sensor. Generally, a gradient of concentration or partial pressure of the analyte, frequently but not necessarily a gaseous substance, such as molecular oxygen, hydrogen, ozone, carbon dioxide etc., is established across the membrane located between the fluid and the interior of the sensor. The flux of analyte diffusing across the membrane is then measured and related to the concentration or partial pressure of the analyte in the external phase or probe assuming that the membrane alone is responsible for limitation of the flux. The specific type of measuring means used depends upon the analytical method employed and is not a feature of the present invention.

The feature common to substantially all types of MES is their capacity to generate a signal related to the concentration of the analyte which frequently is a normally (i.e. under the pressure and temperature conditions of the measurement) gaseous substance of analytical interest in a fluid external phase which, in turn, may be liquid or gaseous.

The MES may, or may not, provide for selectively detecting or sensing more than one analyte (e.g. oxygen and hydrogen in mutual presence, cf. EP-A-0293541 or U.S. Pat. No. 4906339).

The membrane of a MES is frequently characterized as being "semipermeable" in the sense of permitting permeation of the analyte but substantially precluding permeation of a liquid or, sometimes, of another gaseous constituent of the external phase. Typical examples of such membranes are films or self-supporting strata made of organic polymers, e.g. of polytetrafluoroethylene, polyethylene, polyvinylidene chloride, or the like organic polymers, but membranes of other materials, such as foils of palladium for sensing of $H_2$, may satisfy the requirements of a semipermeable membrane herein.

In any case, semipermeability of the membrane and even impermeability to liquids is not believed to be a critical aspect of the present invention because no liquid constituent might be present in the external sample and because the sensing method might be based upon differing diffusion rates of different gases. In such cases the function of the membrane is that of providing a diffusion impedance.

Generally, the operation of a MES is "destructive" (understood in the sense of "invasive" as opposed to "non-invasive") because the composition of the external phase will change in the close vicinity of the membrane due to "depletion", i.e. permeation or "extraction" of one or more analyte(s) from the external phase through the membrane into the sensing device where the analyte may be "consumed", i.e. converted into a different chemical species, vented, or removed from the system by another method. As a result, the external phase in close vicinity of the membrane becomes depleted of the analyte, and a certain "flow demand", or "minimum flow rate" discussed in more detail below, of the external phase will be required to achieve an acceptable fraction (say 99%) of the signal that would represent the theoretical or undepleted concentration of the analyte in the body of the external phase.

Typically, membranes of such types of MES are disk shaped films or foils sealed to the body of the sensor by a holding ring (cf. EP-A-0043611), and are supported from within the sensor but are necessarily unencumbered or only weakly supported on the external or sample side because of the need to allow unimpeded access of flowing external phase to the membrane.

Definition of Terms

When the analyte is removed or "extracted" from the external phase through the membrane into the sensor, the concentration of the analyte in the external phase in the near vicinity of the membrane diminishes. This, in turn, leads to a drop of the signal generated by the sensing device within the sensor. The extent of this change depends upon the balance between the rate of entry of the analyte into the sensor, and the rate of replenishment of the analyte by conviction or diffusion from other regions of the external phase. In gaseous fluids, diffusion alone is usually sufficient to ensure that the composition of the external phase changes by a negligible amount (e.g. <1%) only. Then, the above-mentioned assumption that the membrane alone controls the flux of analyte through the membrane is justified.

In liquids, on the other hand, transport processes are much slower than in gases, because of the greater viscosity of liquids. In such media, convection is a much more efficient means of transport of analyte to the membrane than is diffusion. Hence, there is a dependence of the concentration of the analyte in those regions of the liquid adjacent the membrane, and of the signal generated by the sensor upon the rate of convective flow of the liquid past the sensor. At an "infinite" flow rate, the concentration of the analyte would be unmodified, and the signal would take a maximum value characteristic of the "bulk" concentration. Again, the above assumption would be justified.

Accordingly, the term "flow demand" of the sensor as used herein is intended to indicate the minimum flow rate of the liquid required to make the signal approach the flow-independent limit within a specified error (usually 1%). Only for flow rates beyond the flow demand is the assumption of membrane control of analyte supply to the sensor really valid.

According to the art (cf. Hale, J. M., "Factors influencing the stability of polarographic oxygen sensors" in "Polarographic Oxygen Sensors . . . ", Gnaiger E and Forstner H.

(editors), Springer Verlag 1983) this phenomenon may be quantified by expressing the flux of a gaseous analyte into the MES by $$J_g = f_g/(R_l + R_m) \qquad \text{(Eq. 1)}$$

where $J_g$ represents the flow of gas, $f_g$ its fugacity in the bulk of the fluid external phase, $R_l$ the diffusion impedance in the fluid external phase and $R_m$ that in the membrane. Clearly, the requirement that the sensor signal be independent of flow may alternatively be articulated as a requirement that the diffusion impedance in a liquid external phase be negligible in comparison with the impedance of the membrane.

The impedances may be further expressed as:

$$R_i = z_i/(D_i \cdot S_i) \qquad \text{(Eq. 2)}$$

where $D_i$ is the diffusion coefficient, $S_i$ the solubility of the gaseous analyte, and $z_i$ the thickness of the layer identified by subscript "i", "m" standing for membrane and "1" for liquid external phase. As a result, the "negligible impedance" criterion is equivalent to the requirement that the thickness of the hydrodynamic diffusion layer in the liquid external phase $z_l$ be much less than the critical thickness $z_c$ defined by $$z_c = z_m \cdot D_l \cdot S_l/(D_m \cdot S_m) \qquad \text{(Eq. 3)}$$

This critical thickness is constant for virtually any reasonable combination of gaseous analyte(s), membrane and liquid external phase.

Generally, the thickness $z_l$ of the hydrodynamic diffusion layer decreases with flow velocity even though a precise mathematical relation between these quantities may depend upon the specific geometrical configuration. However, when assuming laminar flow and for a simple geometry, quantification is possible. For example, in a tube of circular cross section the relation can be expressed as $$z_l \propto 1/V^{1/3} \qquad \text{(Eq. 4)}$$

where V is the flow velocity.

There are two main methods of measuring the concentration of an analyte with an MES:

(A) The sensor is immersed directly into the flowing liquid; this method is also termed "in-line" measurement; in this instance, the flow demand can be regarded as a critical linear velocity of the liquid, e.g. in cm per second but flow demand is not a controllable parameter of in-line measurement since it's satisfaction is generally assumed.

(B) The sensor is located within an enclosed space ("flow chamber") having an entrance port and an exit port for passing the sample fluid or liquid, respectively, through the flow chamber; this method is also termed "off-line" measurement and the flow demand could be expressed in terms of a volume per time unit or flow rate, e.g. millilitres (ml) per minute (min). Again, satisfaction of flow demand is generally assumed in off-line measurement.

Generally, "flow demand" is not normally a quantifiable parameter of prior art operation of an MES, and if sample depletion is a problem, such as in-vivo blood analysis, correction is normally made by measurement during a limited time span and extrapolating to infinite time ("dynamic measurements").

OBJECTS AND BRIEF SUMMARY OF THE INVENTION

Accordingly, it is a main object of the invention to provide for a membrane enclosed sensor (MES) or cell in which a substantial flow demand can be controlled and/or maintained at a predetermined value.

Another object of the invention is a device for use in combination with an MES such that a prior art MES can be made to operate to satisfy a predetermined flow demand.

A further object of the invention is a method of operating an MES so as to achieve a predetermined flow demand. Other objects will become apparent as the specification proceeds.

It has been found that the above objects and further advantages will be achieved, according to a general first embodiment of the invention, in a membrane-enclosed sensor by providing a coiled channel at the interface between the outer surface of the membrane and the external phase, said channel having an inlet and an outlet for passing the external phase in contact with the membrane along said coiled channel.

In other words, the invention provides structural and operational means to channel the flux of the external sample phase into a small cross-section contacting the membrane so as to raise the linear velocity of the external phase and reducing the thickness of the hydrodynamic and diffusion boundary layers within the external phase at the membrane surface so as to provide for improvement of the efficiency of convective transport of analyte to the membrane.

BRIEF DISCUSSION OF PREFERRED EMBODIMENTS

According to a preferred embodiment, the sensor according to the invention comprises: a membrane that is substantially impermeable to a liquid external phase but permeable to at least one fluid species of analytical interest; and at least one sensing device for a characteristic parameter of said at least one fluid species of analytical interest;

said membrane forming at said interface a separation between said Sensing device and said external phase; said membrane having an outer surface for exposure to said external phase, said outer surface having a largest cross dimension;

said sensor comprising a flow device having an inlet end and an outlet end connected with said coiled channel; said coiled channel having a length extending from said inlet end to said outlet end of said flow device, and said length of said channel being at least about 5 times and preferably at least about 10 greater than the largest cross dimension of the outer surface of said membrane.

Preferably, the coiled channel has an essentially spiral form extending from one end of the spiral to another end thereof, the inlet end being located at said one end of said spiral while said outlet end is located at said other end of said spiral. Also, it is preferred that the outer surface of the membrane has an essentially circular shape.

According to a second general embodiment, the invention provides a flow control element for use with a membrane-enclosed sensor provided with a semipermeable membrane having an outer surface for exposure to an external phase of analytical interest and a largest linear cross dimension; the flow control element according to the present invention has at least one elongated recess capable of forming a coiled channel when in contact with said outer surface of said membrane; said elongated recess having a length extending from an inlet to an outlet of said element, and said length of said recess being at least about 5 times and preferably at least about 10 times greater than the said largest linear cross dimension of the outer surface of said membrane. Also, it is preferred for many purposes that the elongated recess of the flow control element has an essentially spiral form extending from one end of the spiral to another end thereof, said inlet of said element being located near said one end of said spiral while said outlet is located near said other end of said spiral.

According to a third embodiment, the invention provides for a method of operating a membrane enclosed sensor of the type comprising:

a membrane that is substantially impermeable to a liquid external phase but permeable to at least one species of analytical interest;

at least one sensing device for a characteristic parameter of said at least one species of analytical interest;

said membrane forming a separation between said sensing device and a normally liquid external phase suspected of containing said at least one species of analytical interest;

said membrane having an outer surface for exposure to said external phase, and said outer surface having a largest linear cross dimension;

said method comprising the step of providing at least one coiled channel for passing said external phase in contact with said outer surface of said membrane.

Preferably, the coiled channel for use in the method according to the invention has a length extending from an inlet end to an outlet end of said channel, and said length being at least about 5 times and preferably at least about 10 times greater than the largest linear cross dimension of the outer surface of the membrane.

As will be apparent to those experienced in the art, the sensor as well as the flow control element and the method according to the invention are of use mainly for analytic methods of the "invasive" type, in other words where at least a portion of the analytic species of interest is removed from the external medium, i.e. depletion of the external phase occurring at least in the vicinity of the membrane.

An essential advantage of the present invention is that it provides for a reduction of the volume flow demand, that is, it reduces the flow rate of a liquid external phase that contains the analyte through a flow chamber, which flow rate is needed to reach the flow independent limit of the signal generated by the sensor.

Another advantage of the invention is that membranes of higher permeability may be used on the sensor at any particular flow rate, shifting the range of concentrations measurable with the sensor to lower concentrations.

A further advantage is that the volume of liquid samples required in order to effect a measurement is reduced. The reason is that the lower flow demand multiplied by the stabilization time needed by the sensor represents a smaller volume of sample.

Yet another advantage of the invention is that it provides a robust protection for the sample side of the membrane, so avoiding damage from sudden pressure variations.

The present invention is of primary importance for sensors where the volume flow demand of the sensor is substantial, particularly sensors that have an essentially cylindrical symmetry including an essentially disk shaped membrane. While the following description will deal mainly with this type of sensor it is to be understood that the invention is not restricted to such a sensor embodiment.

DETAILED DESCRIPTION OF THE PREFERRED EMBODIMENTS

Figure 1:
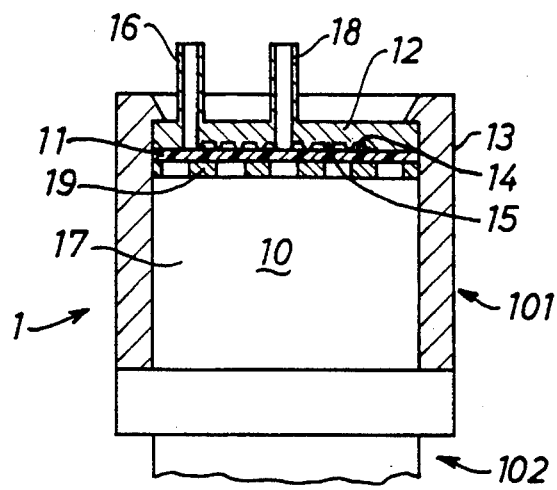

The term "coiled channel" as used herein is intended to include any type of elongated conduit that can be formed between a membrane and an elongated recess provided at the surface of a generally flat shape closely fitting the outer surface of the membrane, i.e. that exposed directly to the external phase, when in sealing contact with said membrane surface; by "coiled" it is meant that the length of the recess or channel should be greater than the largest cross-sectional dimension of the exposed membrane surface; generally, the length of the coiled channel or recess will be at least about 5 times greater than the largest cross-sectional dimension of the exposed membrane surface and, in typical cases, will be at least about 10 times greater.

The radial width of the channel or recess, on the other hand, will generally be substantially uniform over the length of the channel and will generally be dependent upon the exposed surface area of membrane, the width of the sealing margin between the coils and the fact that the flow resistance of the channel for the external medium should be low enough to permit reliable and reproducible operation under the conditions of measurements, including as main factors (a) the viscosity of the external phase at the measuring temperature, (b) the presence and size of suspended particles, if any, in the external phase, (c) the pressure of the external phase within the channel, and (d) the stability of the membrane in operative position.

As a general rule for many typical applications, the radial width of the channel should not be smaller than about 5% of the largest cross-dimension of the membrane; by the same token, the axial width, or "depth" of the channel or recess should not exceed twice the radial width and preferably does not exceed the radial width. In absolute terms, a typical range of the radial width of the recess or channel is between about 0.5 and 5 mm.

As indicated above, the channel is generally formed by the coiled recess and the adjacent surface of the membrane. A margin, e.g. a ridge or band protruding between the recessed coils is provided to separate adjacent coils. The radial width of the margin between adjacent coils will generally be made as small as feasible in view of the need to prevent "shorts", i.e. direct penetration of the external phase from one coil to the adjacent coil other than by passage through the channel. Typically, the margin portion of the flow element will have a radial width between about 0.5 and 5 mm. The cross-sectional shape (viewed in an axial plane) of the recess or channel is not believed to be critical and may depend upon the machining or moulding method used to produce the flow element which, in turn, may be made of a relatively rigid organic polymer, such as polyacetals, polycarbonates, polyacrylics, etc., or of a suitable metal, such as stainless steel, titanium or other structural material that is inert under the conditions of operation and has a sufficient rigidity. Triangular or semi-circular cross-sections can be mentioned as examples for the cross-sectional shape of the recess or channel with the membrane serving as the geometric base of the channel's cross-sectional shape.

BRIEF DISCUSSION OF THE DRAWINGS

Figure 2:
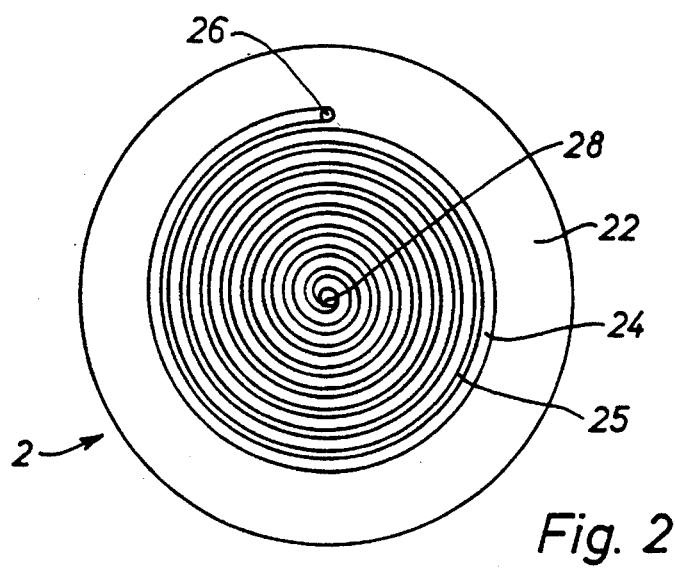
Figure 3:
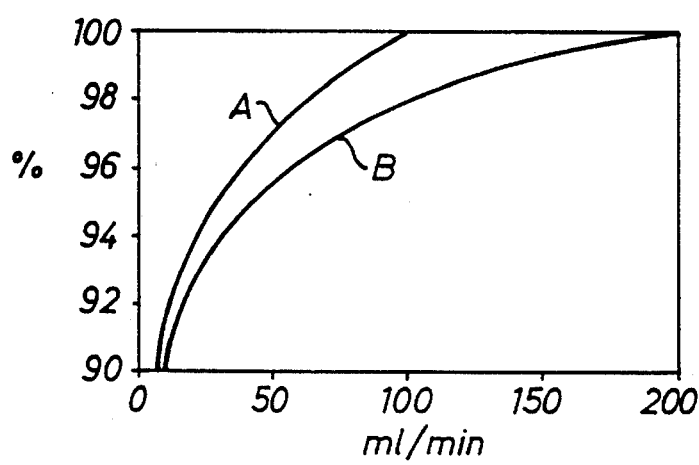

The invention will be illustrated by way of example, not limitation, in the annexed drawing in which FIG. 1 is a diagrammatic sectional view of the head of a sensor according to the invention;

FIG. 2 is a diagrammatic top view of the flow element according to the invention, seen from that side of the flow element that carries the coiled recess; and FIG. 3 is a diagram of time versus flow rate when operating an example of the method according to the invention.

DETAILED DISCUSSION OF THE DRAWINGS

FIG. 1 illustrates the upper portion 101 of a generally cylindrical sensor I connected to the stem or body 102 thereof. Head 13 holds flow device 12 provided at its inner surface 14 with a spiroidally coiled recess 15, the ends of which are connected with an inlet conduit 16 and an outlet conduit 18. Either conduit 16 or 18 is connected to a pump (not shown) for conveying the external phase through the channel formed between the coiled recess and the adjacent surface portions of the outer side of membrane 11. Recessed surface 14 is held in sealing engagement with membrane 11 which, in turn, is supported at its lower surface by a perforated support face 19 of sensor 1.

A sensing or measuring device (not shown) of the type known for membrane enclosed sensors is provided at the interior 10 of head 13 to produce a signal depending upon the (static) presence, or dynamic flux rate, of the analyte, depending upon the method of measurement.

FIG. 2 shows a diagrammatic top view of a flow device 2 (reference numeral 12 in FIG. 1) consisting essentially of a disc 22 of a rigid structural material (such as, for example, polyacetal, polyamide, ABS, polysulfon, polyetherether ketone, polytetrafluoroethylene, polymethylmethacrylate, or metals such as steel or titanium) provided with a spiroidally coiled recess 24 extending from the inlet end 26 to the outlet end 28 but it is not believed to be critical which port is used as an entry and which as an outlet. Recess 24 is formed by moulding such that a spiroidal margin 25 separates adjacent coils of recess 24.

Sealing effectiveness of the margin 25 will depend upon the sealing capacity of membrane 11 supported by support face 19 (FIG. 1.) as well as the pressure that is effected between flow element 12 recess and the adjacent surface of membrane 11. Care should be taken, in any case, to prevent damage if very thin membranes are used. Also, the pressure used to convey the external phase through the coiled channel should be considered in that connection. Typically, such pressure is in the range of from about 1 to about 10 kg/cm$^2$.

Generally, the sealingly effective surface portions, or spiroidal margin 25, of flow element 12 will closely follow the shape of membrane 11 and its support face 19. Accordingly, the substantially plane shape of membrane 11, supporting face 19 and flow element 12 is by no means critical, and a calotte-shaped convex form of support face 19 with a matching concave shape at the membrane-contacting side of the flow element may be preferred for many purposes.

While an essentially circular shape of flow device 2 and a spiroidal shape of recess 24 is preferred for many uses, it might have a rectangular or polygonal shape, depending upon the structure of the sensor, and the coiled recess need not be spiroidal but could be arranged in the form of a path with angular path changes around a center or in a back-and-forth or zig-zag shape from top to bottom.

As will be apparent from the above, the invention may be practised in connection with a sensor according to the invention as manufactured, or as a flow element shaped to match a commercially available prior art sensor.

The invention will be further illustrated by means of the following non-limiting examples.

EXAMPLE 1

A flow element 2 was constructed in polyacetal having the form depicted in plan view in FIG. 2 and in side elevation in FIG. 1. A spiral channel connects the entrance port (2 mm diameter) to the exit port—whether these are selected to be the central and excentric port (at 1 cm radial distance from the center), respectively, or vice versa, is not critical. Liquid external phase entrained in the channel has an average velocity expressed as the volume flow rate divided by the cross sectional area of the channel.

The channel was isosceles triangular in section, with dimensions:

Width (radially measured)=1 mm;
Depth (axially measured)=0.6 mm

Hence, its cross sectional area was 0.003 cm$^2$. At a typical flow rate of 250 cm$^3$ per minute, the pressure drop was 0.2 bars and the average linear velocity of liquid in the channel was 13.9 meters per second.

This contrasts with the usual chamber space provided in standard flow chamber designs, in which the flow splays radially outward from a central orifice, in a cylindrically symmetrical chamber space of which the membrane forms one wall and the body of the flow chamber the other, towards the exit at the periphery. Typically the separation "d" of these parallel walls would be about 0.6 mm. Accordingly, the cross- sectional area through which the liquid external phase flows is proportional to the radius "r" so that its velocity "v" falls, and the hydrodynamic diffusion layer thickness broadens as the distance from the entrance increases:

$$v = V/2\pi r d \qquad (Eq. 5)$$

where V represents the volume flow rate.

In this case, if the depth of the channel and the flow rate are as before and the exit is at a radius of 1 cm, the linear velocity of liquid over the membrane surface is only 11 centimeters per second at the periphery, i.e. 125 times slower.

A 125 fold increase in speed of flow in a tube would lead to a 5 times ($1/V^{1/3}$) decrease in the average thickness of the diffusion layer and a 5 times increase in the efficiency of convective supply of gaseous analyte to the membrane. A similar factor is expected to apply in the case of a triangular channel, but to the best of applicants knowledge, the case of the "radial" channel has never been considered or discussed in the art.

EXAMPLE 2

The advantageous effects of the sensor and flow device illustrated in FIGS. 1 and 2 can be appreciated from FIG. 3 derived from measurements of the electric current, a direct measure of the flux of gas through the membrane, delivered by an electrochemical oxygen sensor of the Clark design (as supplied by Orbisphere, Geneva, Switzerland; Model 31120, electrode radius 0.316 cm, flow velocity at the edge of the electrode at 250 cm$^3$/min=35 centimeters/sec) exposed to air saturated water at 25° C., as a function of flow rate of the water.

The membrane material was a perfluoroalkoxy polymer film of 25 μm thickness purchased from E.I. Du Pont et de Nemours. The sensor current is expressed as a percentage of the current (≅25 μA) delivered by the same sensor when exposed to 100% humid air at the same temperature. As is known to those experienced in the art, this latter current should be identical to the limiting current which could be observed in water flowing at "infinite" velocity. In the region where the current is varying, the diffusion within the hydrodynamic boundary layer is partly responsible for limitation of the magnitude of the current. However, once the current has reached a plateau, the "impedance" represented by diffusion in the water is negligible in comparison to the impedance of the membrane.

The diagram of FIG. 3 shows curves A and B indicating the true indication in percent (on the ordinate) versus flow rate (ml/min) of air saturated water. Curves A and B compare the current obtained at 25° C. from the sensor fitted with a flow device according to the invention with that of the same sensor without a flow device located in a conventional flow chamber of a generally radial construction and operated under otherwise identical conditions. With the flow device according to the invention, the flow demand is halved.

It is to be noticed that the damage-sensitive membrane of the oxygen sensor is safely protected by the flow device according to the invention. Were a similar protection provided on the sensor when in the conventional flow chamber, there would be further interference with convective transport and consequent increase in flow demand. It will be apparent to those experienced in the art that various modifications of the above illustrations are possible within the scope of the invention as defined in the attached claims.

Accordingly, what is claimed is:

1. A membrane-enclosed sensor having a membrane for exposure to a fluid external phase of analytical interest at an interface between said fluid phase and said membrane; said sensor comprising a coiled channel at said interface, said channel having an inlet end as well as an outlet end for passing said external phase in contact with said membrane through said coiled channel, said coiled channel increasing velocity of said external phase when said external phase is passed therethrough and reducing the thickness of the hydrodynamic and diffusion boundary layers within the external phase at the membrane interface so as to provide for improvement of the efficiency of convective transport of analyte to the membrane.

2. The sensor of claim 1 comprising a membrane that is substantially impermeable to a liquid external phase but permeable to at least one fluid species of analytical interest, and at least one sensing device for a characteristic parameter of said at least one fluid species of analytical interest;

said membrane forming at said interface a separation between said Sensing device and said external phase; said membrane having an outer surface for exposure to said external phase, said outer surface having a largest cross dimension;

said sensor comprising a flow device having an inlet end and an outlet end connected with said coiled channel; said coiled channel having a length extending from said inlet end to said outlet end of said flow device, and said length of said channel being at least about 5 times greater than said largest cross dimension of said outer surface of said membrane.

3. The sensor of claim 2 wherein said coiled channel has an essentially spiral form extending from one end of said spiral to another end of said spiral, said inlet end being provided at said one end of said spiral while said outlet end is provided at said other end of said spiral.

4. The sensor of claim 2 wherein said outer surface of said membrane has an essentially circular shape.

5. The sensor of of claim 2 wherein said length of said coiled channel is at least about 10 times greater than said largest linear cross dimension of said outer surface of said membrane.

6. A flow control element for use with a membrane-enclosed sensor provided with a semipermeable membrane having an outer surface for exposure to an external phase of analytical interest and a largest linear cross dimension;

said flow control element having at least one elongated recess capable of forming a coiled channel when in contact with said outer surface of said membrane;

said elongated recess having a length extending from an inlet to an outlet of said element, and said length of said recess being at least about 5 times greater than said largest linear cross dimension of said outer surface of said membrane, said coiled channel increasing velocity of said external phase when said external phase is passed therethrough and reducing the thickness of the hydrodynamic and diffusion boundary layers within the external phase at the membrane outer surface so as to provide for improvement of the efficiency of convective transport of analyte to the membrane.

7. The element of claim 6 wherein said elongated recess has an essentially spiral form extending from one end of said spiral to another end of said spiral, said inlet of said element being provided at said one end of said spiral while said outlet is provided at said other end of said spiral.

8. A method of operating a membrane enclosed sensor of the type comprising:

a membrane that is substantially impermeable to a liquid external phase but permeable to at least one species of analytical interest;

at least one sensing device for a characteristic parameter of said at least one species of analytical interest;

said membrane forming a separation between said sensing device and a normally liquid external phase suspected of containing said at least one species of analytical interest; said membrane having an outer surface for exposure to said external phase, and said outer surface having a largest linear cross dimension;

said method comprising the step of providing at least one coiled channel for passing said external phase in contact with said outer surface of said membrane, said coiled channel increasing velocity of said external phase when said external phase is passed therethrough and reducing the thickness of the hydrodynamic and diffusion boundary layers within the external phase at the membrane outer surface so as to provide for improvement of the efficiency of convective transport of analyte to the membrane.

9. The method of claim 8 wherein said coiled channel has a length extending from an inlet end to an outlet end of said channel, and said length being at least about 10 times greater than said largest linear cross dimension of said outer surface of said membrane.

10. The method of claim 9 wherein said species of analytic interest is depleted in said external phase in the vicinity of said membrane.

11. A membrane-enclosed sensor as in claim 1, wherein said interface is substantially flat.

12. A membrane-enclosed sensor as in claim 1, wherein said coiled channel is substantially planar.

13. A membrane-enclosed sensor as in claim 1, wherein said membrane is disk-shaped.

14. A flow control element as in claim 6, wherein said membrane outer surface is substantially flat.

15. A flow control element as in claim 6, wherein said coiled channel is substantially planar.

16. A flow control element as in claim 6, wherein said membrane is disk-shaped.

17. A method as in claim 8, wherein said membrane outer surface is substantially flat.

18. A method as in claim 8, wherein said coiled channel is substantially planar.

19. A method as in claim 8, wherein said membrane is disk-shaped.

* * * * *